United States Patent [19]

Hoffmann et al.

[11] Patent Number: 6,103,251
[45] Date of Patent: Aug. 15, 2000

[54] INJECTION METHOD FOR ADMINISTERING MICROPARTICLES CONTAINING ACTIVE SUBSTANCES TO PLANTS

[75] Inventors: Hans-Rainer Hoffmann, Neuwied; Malgorzata Kloczko, Linz; Michael Roreger, Neuwied, all of Germany

[73] Assignee: LTS Lohmann Therapie-Systeme GmbH, Neuwied, Germany

[21] Appl. No.: 09/155,021

[22] PCT Filed: Feb. 15, 1997

[86] PCT No.: PCT/EP97/00721

§ 371 Date: Mar. 15, 1999

§ 102(e) Date: Mar. 15, 1999

[87] PCT Pub. No.: WO97/34474

PCT Pub. Date: Sep. 25, 1997

[30] Foreign Application Priority Data

Mar. 16, 1996 [DE] Germany .................. 196 10 398

[51] Int. Cl.$^7$ .................................................. A01N 25/08
[52] U.S. Cl. ..................... 424/405; 424/406; 424/408; 424/417; 424/490; 424/493; 424/494; 424/496; 424/497; 424/498; 424/500; 424/501; 424/502; 424/499; 47/57.5; 504/116

[58] Field of Search ................. 504/116–118, 162, 504/174, 184, 187–189; 424/405, 406, 408, 417–421, 490–502, DIG. 8; 47/57.5

[56] References Cited

U.S. PATENT DOCUMENTS

| | | | |
|---|---|---|---|
| 3,069,809 | 12/1962 | Simmons | 47/57.5 |
| 3,482,353 | 12/1969 | Fisher et al. | 47/9 |
| 4,690,682 | 9/1987 | Lim . | |
| 5,275,819 | 1/1994 | Amer . | |

*Primary Examiner*—Neil S. Levy
*Attorney, Agent, or Firm*—James Klaniecki; Ann W. Speckman

[57] ABSTRACT

A process for the administration of a flowable solid, semisolid, or liquid medium exhibiting a controlled release of at least one active substance to plants by means of injection using needle-free, pressure-actuated devices is characterized in that the medium comprises active substance-containing microparticles of a maximum size of 100 $\mu$m including the following components:

a) 0.5–70%-wt. of at least one active substance, b) 10–70%-wt. of at least one biodegradable polymer, c) up to 20%-wt. of formulation adjuvants.

4 Claims, No Drawings

INJECTION METHOD FOR ADMINISTERING MICROPARTICLES CONTAINING ACTIVE SUBSTANCES TO PLANTS

The present invention relates to a process for the administration of active substance-containing flowable, solid, semisolid, or liquid media having a controlled release of at least one active substance to plants by means of injection using needle-free pressure-actuated devices.

It is known in the art to use needle-free pressure-actuated injection devices for the administration of bioactive substances to plants. For example, DE-OS 25 55 092 describes the use of pressure injectors with a plurality of injection nozzles for the treatment of plants. U.S. Pat. No. 3,069,809 also describes pressure-actuated injection devices without injection cannulae by means of which active substances are brought into plants.

The use of needle-free high-pressure injectors represents a favorable alternative to conventional injection processes. Owing to the fact that relatively high-viscous media can be injected by means of the needle-free injection technique, it is also possible to inject polymeric liquids into plants to be treated. This is of particular importance since the injection medium may be a formulation having controlled release properties. Another advantage of this needle-free injection technique and its corresponding devices, which are capable of creating very high pressures, is the possibility of treating plants having a relatively thick wood-body.

It is also known to administer controlled-release active substance preparations to plants by injecting particulate active substance carriers. U.S. Pat. No. 5 275 819 describes a feed system for biologically active substances to living organisms (humans, animals, plants). This feed system is to be administered enterically (injectable or implantable). The known device consists of a plurality of natural active substance-containing microbeads (microspheres), i.e. those occurring in animal or plant organisms, which release active substances in a controlled manner when in use.

U.S. Pat. No. 4 690 682 describes an active substance delivery system achieving a delayed active substance release in human, animal or plant bodies. In this case, injectable active substance-containing microcapsuies are concerned which have a size between 0.1 and 3.0 $\mu$m and a porous, release-controlling membrane.

Both documents point out the advantages of microencapsulating active substances in the administration to living organisms, inter alia to plants; these in particular include increase in stability, fixation of volatile substances, and reduction of toxicity. In particular toxicity reduction is of decisive importance for an administration form when plants are injected with active substances of relatively high phytotoxic potential; this is documented in relevant literature (F. Müller, "Phytopharmakologie"), for example.

Moreover, microencapsulating the injectable substances ensures that they are not directly influenced by the plant metabolism. It is known that there are several factors impairing or limiting the distribution of organic compounds in the plant, in particular when it takes place in the phloem. These factors in particular include adsorption, formation of complexes and conjugates, and release from the sieve tubes into neighboring sieve parenchyma cells which may have a detrimental effect on the transport of exogenous substances.

However, it is pointed out in this context that—in contrast to external applications such as spraying processes— the risks connected with the injection of encapsulated active substances cannot completely be excluded. The properties of the polymeric starting materials used, e.g., low decomposition rate, plant intolerance, as well as the particle characteristics, e.g., particle diameter, represent factors which may have a negative effect on the mobility of the substances which are phloem-mobile per se.

However, to develop a protective or therapeutic effect active substances must reach their sites of action in sufficient amounts. As a consequence, capability of being translocated is of particular importance.

To distribute the injected microparticles efficiently in conductive paths of the plant, their size and/or chemical composition as well as the insertion depth is of importance. This is particularly true for plants having secondary growth in thickness, such as woody plants wherein primary and secondary wood parenchyma rays, in which mainly organic compounds are transported, run through the wood at differing depths. To penetrate a thick wood-body often having several annual rings, and to control the insertion depth, suitable feed systems are required. High-pressure injectors known in the art are used as suitable feed systems for this purpose.

In the application of active substance-containing microparticles to plants most attention has been paid to their use on plant surfaces rather than to their enteric administration, such as injection or implantation. For this reason, the significance of suitable polymeric starting materials has not sufficiently been examined or described in the art. In this connection, the state of the art merely mentions natural microspheres (pollen, spores) and natural or synthetic polysaccharides (for example, sodium alginate, calcium alginate, pectins, carragheenan).

There is scarce knowledge of the influence of particle size on the particles' capability of being translocated. It cannot be excluded that an increasing particle diameter impairs the mobility of the particulate active substance carriers in the plant.

At present, there are no satisfactory solutions meeting the demand for particulate injection systems providing controlled active substance release within plant organisms.

It is accordingly the object of the present invention to provide a process which can realize the above-mentioned goal of efficiently distributing the injected microparticles within paths of conduction of a plant. According to the present invention this object is achieved by a process according to the features of claim 1.

The present invention and its advantages will be illustrated in the following.

The present invention relates to a process for the administration of active substance-containing microparticles having a maximum size of 100 $\mu$m to release an effective amount of the active substance within a predetermined period by means of injection using needle-free, pressure-actuated devices, the particles comprising one or several active substances in admixture with one or several biodegradable polymers or copolymers as well as suitable additives in the following composition:

a) 0.5–70%-wt. of at least one active substance,
b) 10–70%-wt. of at least one biodegradable polymer,
c) up to 20%-wt. of formulation aids.

According to the present invention the term"microparticles" means both real microcapsules, i.e., microparticles wherein an active substance core is surrounded by a polymer matrix, and monolithic microcapsules (microspheres), wherein an active substance is homogeneously distributed within a polymer matrix. According to the present invention the term "biologically degradable", which is equivalent to "biodegradable", means "degradable by stimulation through a biologically active environment". These mean compounds which are both available to the metabolism of higher plants and metabolizable by microbes. Any biodegradable polymer may be used to manufacture the microparticles used in the process according to the present invention.

Examples include:

aliphatic polyesters, such as poly-E-caprolactone (TONE® P787), poly-3-hydroxybutanoic acid copolymers, poly-3-hydroxyvaleric acid copolymers, polyethylene succinate, polybutylene succinate (BIONOLLE®)

polysaccharides, such as starch, sodium alginate (MANUCOL® LB) calcium alginate, carragheenan, and pectins cellulose and its derivatives, e.g., mixed esters, cellulose acetate butyrate polylactic acid and polyglycolic acid and their derivatives, such as poly-L-lactide, poly-D,L,-lactide, and lactide-glycolide copolymers.

The ratio between the polymeric active substance carrier material and the active substances may vary according to the desired effect; however, it must correspond to the composition as defined in claim 1.

A preferred embodiment of the particles used in the process according to the present invention has the following components:

a) 35–60%-wt. of an active substance
b) 45–50%-wt. of a biodegradable polymer
c) 5–10%-wt. of additives.

Biological degradation leads to simultaneous active substance release, and it is initiated by hydrolytic and/or enzymatic bioerosion in the plant. Degradation of the products applied by means of the process according to the present invention mainly results in fragments that are known as to their biocompatibility and which can be metabolized in natural metabolic pathways of the plant. Intensity and scope of particle decomposition in the plant organism depend on the kind of polymeric materials used. Thus, their period of degradation can be adapted to the indicated requirements by adequate choice of starting materials. This property particularly suits the diversity of individually required active substance supply found in plant cultivation. For example, in diseases involving a high degree of initial infestation, water-soluble particulate active substance carriers, e.g., made of specific polysaccharides, may be used which are subject to a relatively rapid hydrolytic degradation under the conditions prevailing in the conductive paths of the plant. The resulting rapid active substance release results in the desired rapid onset of action.

Active substance release from the microparticles used in the process according to the present invention cannot only take place by bioerosion of the polymeric carrier, but also by diffusion from the polymeric matrix. This is the case in particular when the particles are formed as microspherules, i.e., when the active substance is physically bound in the polymer matrix, without a separate capsule wall. Diffusion-controlled release also takes place when polymeric carrier materials are hydrophobic and less available to the metabolism of higher plants than to that of microorganisms. For example, this applies to polyhydroxy butyrate/polyhydroxy valerate copolymers.

Microcapsules whose matrices remain intact in the use region serve as active substance depot preparation, and they are therefore used in injections for long-term treatments, e.g., in treating the death of elms.

It is essential for the present invention that microparticles having a maximum size of 100 μm be used. The particular advantage of this dimensioning is the particle mobility in the plant that can be achieved thereby. In contrast to prior art particulate active substance carriers whose particle diameters are in the range of 100–3000 μm, the size of the particles used in the injection process according to the present invention corresponds to the average size of plant cells (10–100 μm), Thus their transport in the tissue region which is particularly important for substance distribution in the leaves can considerably be improved because the microbeads are diffusible owing to their relatively small size with given stability. In addition there is the advantage of good mobility in the plant's paths of conduction; this also applies to plants having small-luminal sieve tubes.

Particles based on water-soluble polysaccharides (e.g., starch, alginates, carragheenan and pectins) represent a preferred embodiment of the particulate active substance carriers used in the process according to the present invention. Since their polymer matrix can quite rapidly be converted into osmotically effective substances (e.g., oligosaccharides) within the plant organism, they are preferably transported in the phloem. This is particularly advantageous when growing parts of the plant (meristems) are to be provided with active substances.

Among the active substances which can be injected by means of the process according to the present invention in particulate form, those are to be mentioned which are capable of influencing processes in the animal or plant organism. These primarily include systemically active plant protection agents, for example, insecticides, acaricides, fungicides, and bactericides.

Systemic insecticides include, for example, butocarboxim, dimethoate, fenoxycarb, methamyl, oxamyl, oxydemeton-methyl, pirimicarb, or propoxur.

Systemic acaricides include, for example, clofentizine, fenbutatin oxide, and hexythiazox.

Systemic fungicides include, for example, benomyl, bromuconazole, bitertanole, etaconazole, flusilazol, furalaxyl, fosetyl-Al, imazalil, metalaxyl, penconazole, propiconazole, thiabendazol, triadimefon, triadimenol, or triforine.

Flumequine, for example, is to be mentioned among the systemic bactericides. Systemic growth regulators include, for example, ethephon and β-indolylacetic acid (IAA).

Another advantage achievable by means of the present invention is the fact that the desired injection media may be present both in flowable and solid form. The problem of needle occlusion occurring in conventional injection systems is avoided because here nozzle injection of small-sized microparticles is concerned.

Particularly preferable is a process wherein the composition according to the present invention, which is to be injected, is formulated in liquid vehicles. Suitable liquid vehicles include water, NPKmineral fertilizer solution, and vegetable oils. Water is to be emphasized as particularly preferable.

Adjuvants may be added as required. These may include dispersants, such as polysorbat 80, or thickeners, such as carboxymethylcellulose. Depending on the production method in the process according to the present invention, other adjuvants known to the skilled artisan may also be included.

The present invention will be illustrated by means of the following Example:

EXAMPLE 1

8.8 g poly-D,L-lactide-co-glycolide (molar ratio 50:50) is dissolved in 240 ml dichloromethane and placed in a reaction vessel equipped with a stirrer. 0.36 g of the active substance Al-fosetyl is suspended at a stirring rate of 500 rpm. Subsequently, 54 g sesame oil is progressively added under continued stirring. After complete addition of sesame oil, the mixture comprising the raw microcapsules is continuously dispersed in a thin jet under constant stirring (at 1000 rpm) in 4l of a caprylic-capric acid triglyceride (Miglyol® 812, viscosity 27 to 33 mPa.s) at 20° C. Hardening of the microcapsules takes place within a period of 60 min. The microcapsules thus obtained are filtered off, washed twice with isopropanol, and dried. The particles comprise 2.8%-wt. of the active substance. The average particle diameter amounts to 25.5 µm. Immediately prior to use, 270 mg microcapsules is suspended at 37° C. in 120 ml water. The suspension thus obtained is filled into a pressure-actuated injection device without needle (type Demo-Jet) and injected at a pressure of 8.1 bar into the plant tissue at the basis of a partially lignified biennal sprout (Rubus idaeus).

What is claimed is:

1. A process for the administration of one or more active substances to plants, comprising:

injecting into a plant or plants a flowable solid, semi-solid or liquid medium exhibiting a controlled release of at least one active substance by means of injection using needle-free, pressure-actuated devices, wherein said medium comprises active substance-containing microparticles of a maximum size of 100 µm including the following components:

(a) 0.5–70%-wt. of at least one active substance,
(b) 10–70%-wt. of at least one biodegradable polymer,
(c) up to 20%-wt. of formulation adjuvants.

2. The process according to claim 1, wherein said microparticles are present as a dispersion in an aqueous phase.

3. The process according to any of claims 1 or 2, wherein said biologically degradable polymers are selected from the group consisting of polylactic acid, polyglycolic acid, polylactides as well as their copolymers, cellulose and its derivatives, aliphatic polyesters, and polysaccharides.

4. The process according to claim 3, wherein said polysaccharides comprise water-soluble polysaccharrides, selected from the group consisting of starch, alginic acids and their salts, carragheenans, and pectins.

* * * * *